United States Patent
Chu

(10) Patent No.: US 9,839,717 B2
(45) Date of Patent: Dec. 12, 2017

(54) CYANOACRYLATE ADHESIVE COMPOSITION AND METHOD FOR MAKING THE SAME

(71) Applicant: Fa-Ter Chu, Taipei (TW)

(72) Inventor: Fa-Ter Chu, Taipei (TW)

( * ) Notice: Subject to any disclaimer, the term of this patent is extended or adjusted under 35 U.S.C. 154(b) by 334 days.

(21) Appl. No.: 14/850,198

(22) Filed: Sep. 10, 2015

(65) Prior Publication Data

US 2017/0072092 A1   Mar. 16, 2017

(51) Int. Cl.
*A61K 9/00* (2006.01)
*A61L 24/06* (2006.01)
*A61L 24/04* (2006.01)
*A61L 24/00* (2006.01)

(52) U.S. Cl.
CPC ........... *A61L 24/06* (2013.01); *A61L 24/0021* (2013.01); *A61L 24/0042* (2013.01); *A61L 24/043* (2013.01)

(58) Field of Classification Search
CPC ...................................... A61L 24/06
See application file for complete search history.

(56) References Cited

U.S. PATENT DOCUMENTS

| | | | |
|---|---|---|---|
| 2,721,858 A | 10/1955 | Joyner et al. | |
| 3,254,111 A | 5/1966 | Hawkins et al. | |
| 3,282,773 A | 11/1966 | Wicker, Jr. et al. | |
| 3,527,224 A | 9/1970 | Rabinowitz | |
| 3,564,078 A | 2/1971 | Wicker, Jr. et al. | |
| 3,654,239 A | 4/1972 | McIntire et al. | |
| 3,667,472 A | 6/1972 | Halpern | |
| 4,364,876 A | 12/1982 | Kimura et al. | |
| 7,316,705 B2 | 1/2008 | Kirsch et al. | |
| 8,173,722 B2 | 5/2012 | Baiker et al. | |
| 8,198,344 B2 | 6/2012 | Zhang et al. | |
| 2010/0330027 A1* | 12/2010 | Liu ........................ | A61L 24/06 424/78.35 |

FOREIGN PATENT DOCUMENTS

| | | |
|---|---|---|
| CN | 1362982 A | 8/2002 |
| CN | 104888268 A | 9/2015 |
| TW | 201534359 A | 9/2015 |

OTHER PUBLICATIONS

Taiwanese Search Report dated Jan. 26, 2015, as issued in corresponding Taiwan Patent Application No. 103107494 (6 pages).

* cited by examiner

*Primary Examiner* — Paul Dickinson
(74) *Attorney, Agent, or Firm* — Muncy, Geissler, Olds & Lowe, P.C.

(57) ABSTRACT

The present invention provides a method for making an adhesive composition. An adhesive substrate comprising at least a first cyanoacrylate monomer is provided and then mixed with a thickening agent containing polycyanoacrylate prepared by polymerization of a second cyanoacrylate monomer initiated with an aqueous solution of ammonium hydroxide or alcohol. In light of low boiling point of ammonium hydroxide and alcohol, they can be easily removed by heating at low temperature. As such, conventional premature polymerization of adhesive substrate owing to addition of a thickening agent containing residual accelerators can be overall improved.

20 Claims, No Drawings

CYANOACRYLATE ADHESIVE COMPOSITION AND METHOD FOR MAKING THE SAME

BACKGROUND OF THE INVENTION

1. Field of the Invention

The present invention relates to an adhesive composition, particularly relates to a cyanoacrylate adhesive composition for wound or surgical incision closure and a method for making the same.

2. The Prior Arts

For treatment of small wounds, in general, the anti-inflammatory and anti-microbial drugs are applied so that the wound is gradually closed and healed by natural tissue regrowth. The drugs used here are intended for preventing bacterial infection and easing the pain. However, when the wound is large and deep, rejoining adjacent skins around the wound by sutures is a suitable treatment method to promote prompt wounds healing. Compared to the suturing, the tissue adhesive is currently becoming more popular for wound closure because of its unique properties.

The so-called tissue adhesive is like a glue. When it is used for wound closure, the liquid adhesive is coated on the skin surface adjacent to the wound. Through a curing reaction, the tissue adhesive is solidified and the skins adjacent to the wound can be bonded together by the adhesive, so that the aforementioned wound closure is achieved. Due to the proliferation of epidermal tissue, the cured adhesive would slough off with epidermal cells after about 5-10 days. In some case, the tissue adhesive could be absorbed by the tissue after a period of time. In comparison with the disadvantages of longer operation time and pains associated with the traditional skin suture surgery, utilizing the tissue adhesive for wound closure has the benefits of easy to use, time saving, less pain, and better cosmetic results. As a result, it is the preferred option either for common wound treatment or being an auxiliary treatment for a deep wound. In addition, the tissue adhesive can also be employed to stop the bleeding in ulcer, as an adhesive between the tissue or binding implants to the tissues, etc.

A preferred tissue adhesive has the following characteristics: (1) having sufficient viscosity so that it can be retained on/near the wound and doesn't flow to unexpected location, and it can cure in a short period of time to close the wound promptly; (2) can bond to tissue in the presence of water and having sufficient binding strength, tensile strength and toughness; (3) having excellent biocompatibility, nontoxic and not causing immune responses; (4) being biodegradable; (5) can be used as a scaffold for cell or tissue growth and thus promote healing.

Available tissue adhesives can be divided into three main categories: (1) cyanoacrylate adhesives; (2) fibrin glues; and (3) crosslinked protein glues. Among those, fibrin glues are prepared from animal or human blood. Even though they possess good biocompatibility, there are risks of viral infection. Further, the binding force of fibrin glues is relatively weak with about 3-4 $N/cm^2$, which is a disadvantage for tissue adhesive. As for the crosslinked protein glues, although they also have good biocompatibility and biodegradability, the risk of viral infection is the same as fibrin glues. Comparatively, cyanoacrylate adhesives can polymerize rapidly and bond wounds in a few minutes with excellent adhesive performance; thereby they have outstanding hemostasia performance and are able to treat large wounds.

Cyanoacrylate adhesives are generally applied in monomeric form for wound closure. The cyanoacrylate monomers normally start anionic polymerization in the presence of water on the skin surface forming the desired adhesive bond with the skin. However, the monomeric form of cyanoacrylate has a very low inherent viscosity which can result in the flow of the adhesive into undesirable areas or into the wound. Other than causing damage to the adjacent tissue, this may affect the wound healing as well. In order to obtain a cyanoacrylate adhesive composition with a higher viscosity, different thickening agents, e.g. polycyanoacrylate, have been added to the adhesive composition. Polycyanoacrylate is generally prepared by initiating polymerization of cyanoacrylate monomers with bicarbonate or the like as an accelerator/initiator. Then a cleaning or neutralization step with an acid is usually required to remove the excess bicarbonate or the like. However, residual accelerators in polycyanoacrylate would cause premature polymerization of the adhesive (containing cyanoacrylate monomers) when the polycyanoacrylate is added therein, and consequently resulting in reduction of bonding strength and the adhesive's performance for wound closure.

SUMMARY OF THE INVENTION

The present invention provides an improved method for making a cyanoacrylate adhesive. The thickening agent employed by the present invention has the characteristic that the accelerator used in the thickening agent can be easily removed. As such, the thickening agent, free of accelerators, can prevent premature polymerization of cyanoacrylate monomers. As a result, the adhesive can retain the bonding strength and its wound closure capability.

In an embodiment of the present invention, a method of making an adhesive composition is provided. The method comprises the steps of: (a) providing an adhesive substrate, the adhesive substrate comprises at least a first cyanoacrylate monomer; (b) providing a thickening agent, the thickening agent comprises at least a polycyanoacrylate, wherein the polycyanoacrylate is prepared by a method comprising the steps of: providing a second cyanoacrylate monomer; adding an aqueous solution of ammonium hydroxide or alcohol into the second cyanoacrylate monomer to initiate polymerization and forming a polymer of the second cyanoacrylate monomer; and heating and drying the polymer of the second cyanoacrylate monomer at 30° C.~100° C. to remove the ammonium hydroxide or the alcohol; and (c) mixing the thickening agent with the adhesive substrate.

In one aspect of the embodiment, the first cyanoacrylate monomer or the second cyanoacrylate monomer may be selected from, but not limited to, the group consisting of alkyl 2-cyanoacrylate, cycloalkyl-2-cyanoacrylate, fluoroalkyl-2-cyanoacrylate, fluorocycloalkyl-2-cyanoacrylate, alkoxyalkyl-2-cyanoacrylate, alkoxycycloalkyl-2-cyanoacrylate, fluoroalkoxyalkyl-2-cyanoacrylate, and mixtures of two or more thereof.

In a preferred aspect of the embodiment, the first cyanoacrylate monomer or the second cyanoacrylate monomer may be selected from, but not limited to, the group consisting of methyl 2-cyanoacrylate, ethyl 2-cyanoacrylate, n-propyl 2-cyanoacrylate, iso-propyl 2-cyanoacrylate, n-butyl 2-cyanoacrylate, iso-butyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate, 2-propoxyethyl 2-cyanoacrylate, and mixtures of two or more thereof.

In another embodiment, the method of making an adhesive composition wherein step (c) further comprises adding at least a plasticizer and then mixing. The plasticizer can be selected from, but not limited to, the group consisting of citric esters, glycerol esters, sebacic esters, fatty acid esters, cellulose esters, polyethylene glycol ethers and mixtures of two or more thereof. In a preferred aspect, the plasticizer may be selected, for example, from the group consisting of glycerol triacetate, glycerol tripropionate, glycerol tributyrate, tricaproin, trivalerin, tricaprin, tributyl 2-acetylcitrate, isobutyl myristate, ethyl myristate, ethyl stearate, methyl sebacate, ethyl sebacate, ethylcellulose, polyethylene glycol diethers, and mixtures thereof. Tributyl 2-acetylcitrate is particularly preferred.

In a further embodiment of the present invention, the thickening agent is about 0.5-25% by weight based on the total weight of the adhesive composition. In a preferred aspect, the thickening agent is about 1-10%, more preferable about 1-5%, by weight based on the total weight of the adhesive composition.

In yet another embodiment of the present invention, the aqueous solution of ammonium hydroxide is about 0.001-1% by weight, preferably about 0.001-0.1% by weight. In another aspect, the weight ratio of ammonium hydroxide to the second cyanoacrylate monomer is about 1:10000 to about 1:100, preferably about 1:10000 to about 1:500.

In a further aspect, the alcohol may be selected from the group consisting of methanol, ethanol, n-propanol, butanol, and mixtures thereof. Because alcohols of lower boiling points can be removed at relatively lower temperature, the alcohol is preferably selected from the group consisting of methanol, ethanol, n-propanol, and mixtures thereof.

In a further aspect, the alcohol is more preferably ethanol, and the ethanol solution can be about 0.1-1.5% by weight, preferably about 0.1-0.6% by weight. In another aspect, the weight ratio of the alcohol to the second cyanoacrylate monomer is about 1:5000 to about 1:100, preferably about 1:5000 to about 1:200.

In another embodiment, the method of making an adhesive composition further comprises the step of adding a colorant, a free radical stabilizer or an anionic stabilizer for desired color and product stability.

In another embodiment, the method of making an adhesive composition further comprises a step of sterilizing the mixture of the thickening agent and the adhesive substrate.

Since ammonium hydroxide and alcohol have relatively low boiling points, they can be readily removed by heating at low temperature when used as an accelerator/initiator for polymerization of cyanoacrylate monomers. As a consequence, the process of removing or neutralizing the accelerator/initiator by conventional means can be eliminated. The thickening agent prepared by the present invention wouldn't contain residual accelerators and would not induce premature polymerization when added into cyanoacrylate monomers. The resulting adhesive composition would retain excellent bonding strength with long shelf life.

DETAILED DESCRIPTION OF THE PREFERRED EMBODIMENT

The following description and examples illustrate a preferred embodiment of the present invention in detail. Those of skill in the art will recognize that there are numerous variations and modifications of this invention encompassed by its scope. Accordingly, the description of a preferred embodiment should not be deemed to limit the scope of the present invention.

For preparing the adhesive composition of the present invention, a thickening agent, i.e. the polymer of the second cyanoacrylate monomer, should be made first. And then the thickening agent, in an amount depending on the demand, is added into the adhesive substrate containing the first cyanoacrylate monomer. After mixing, the resulting adhesive composition with the desired viscosity can be achieved.

The first cyanoacrylate monomer or the second cyanoacrylate monomer may be selected from the group consisting of alkyl 2-cyanoacrylate, cycloalkyl-2-cyanoacrylate, fluoroalkyl- 2-cyanoacrylate, fluorocycloalkyl-2-cyanoacrylate, alkoxyalkyl-2-cyanoacrylate, alkoxycycloalkyl-2-cyanoacrylate, fluoroalkoxyalkyl-2-cyanoacrylate, and mixtures of two or more thereof. In order to obtain the optimum compatibility, e.g., dissolving the polymer of the second cyanoacrylate monomer well in the first cyanoacrylate monomer, the first cyanoacrylate monomer and the second cyanoacrylate monomer are prefer to, but not limited to, the same monomer.

Further, the thickening agent (i.e. the polymer of the second cyanoacrylate monomer) may be poly alkyl 2-cyanoacrylates, poly cycloalkyl-2-cyanoacrylates, poly fluoroalkyl-2-cyanoacrylates, poly fluorocycloalkyl-2-cyanoacrylates, poly alkoxyalkyl-2-cyanoacrylates, poly alkoxycycloalkyl-2-cyanoacrylates, or poly fluoroalkoxyalkyl-2-cyanoacrylates. The preferred weight average molecular weight of the polymers is from about 5,000 to about 4,000,000; more preferably from about 5,000 to about 1,000,000.

For the preparation of the thickening agent, an accelerator/initiator with a low boiling point, e.g., ammonium hydroxide, alcohol, but not limited to, can be added to start the polymerization. Utilizing the property of their relatively low boiling points, ammonium hydroxide or alcohol can evaporate or be easily removed in the following heating procedures. The alcohol can be selected from the group consisting of methanol, ethanol, n-propanol, butanol, and mixtures thereof. The alcohol having a lower boiling point such as methanol, ethanol, n-propanol or mixtures thereof is preferred.

The amount of thickening agent (polycyanoacrylate) intended to be added to the adhesive substrate (cyanoacrylate monomers) is dependent upon the molecular weight of the polymers and the desired viscosity for the adhesive composition. The thickening agent typically may be about 0.5-25% by weight based on the total weight of the adhesive composition, preferably about 1-10% by weight, more preferably about 1-5% by weight.

In addition, a plasticizer can also be added to the mixture of the first cyanoacrylate monomer and the thickening agent for desired viscosity and elasticity. The plasticizer may be selected from, but not limited to, the group consisting of citric esters, glycerol esters, sebacic esters, fatty acid esters, cellulose esters, polyethylene glycol ethers and mixtures of two or more thereof. Preferably, the plasticizer can be selected for example from the group consisting of glycerol triacetate, glycerol tripropionate, glycerol tributyrate, tricaproin, trivalerin, tricaprin, tributyl 2-acetylcitrate, isobutyl myristate, ethyl myristate, ethyl stearate, methyl sebacate, ethyl sebacate, ethylcellulose, polyethylene glycol diethers, and mixtures thereof. Tributyl 2-acetylcitrate is particularly more preferred.

EXAMPLE 1

Preparation of Thickening Agent A

For the preparation of the accelerator, 1800 ml of deionized water was first placed in a 2000 ml beaker, and then 0.7 g (0.04% by weight) of $NH_4OH$ (Showa Chemical Co., Lot. number 111024) was added with a pipette and mixed by stirring for about 5 minutes. Then the second cyanoacrylate monomer, 32 ml of n-butyl cyanoacrylate monomer (nBCA, Chemence Co.), was added into the NH$_4$OH solution drop by drop and mixed by continuous stirring for about 0.5 hour.

The resulting nBCA polymer, namely Thickening Agent A, was decanted and dried in the vacuum oven at 65° C. for 8 hours. The molecular weight of nBCA polymer was measured with a gel permeation chromatography (GPC). Consequently, the molecular weight of nBCA polymer, i.e. Thickening Agent A, is 57,300.

EXAMPLE 2

Preparation of Adhesive A

The first cyanoacrylate monomer, 285 g of 2-octyl cyanoacrylate monomer (2-OCA, the viscosity thereof is 6 cP at 20° C.), was poured into a 1 liter round bottom flask on a heater/mixer and stirred at 200 rpm. 15 g of Thickening Agent A prepared as described in Example 1 was then added slowly into the flask. Then they were mixed at 100° C. for 60 minutes to form Adhesive A. The viscosity of the Adhesive A was measured with a capillary viscometer. The viscosity of the Adhesive A is 43 cP at 20° C.

EXAMPLE 3

Preparation of Adhesive B

The first cyanoacrylate monomer, 285 g of 2-octyl cyanoacrylate monomer (2-OCA, the viscosity thereof is 6 cP at 20° C.), was poured into a 1 liter round bottom flask on a heater/mixer and stirred at 200 rpm. 15 g of Thickening Agent A prepared as described in Example 1 was then added slowly into the flask. 15 g of tributyl 2-acetylcitrate (ATBC, SAFC, Lot number MKBG8107V) was also added slowly subsequently, and then all were mixed at 100° C. for 60 minutes to form Adhesive B. The viscosity of the Adhesive B was measured with a capillary viscometer. The viscosity of the Adhesive B is 39 cP at 20° C.

EXAMPLE 4

Preparation of Thickening Agent B

For the preparation of the accelerator, 1800 ml of deionized water was first placed in a 2000 ml beaker, and then 1 g (0.06% by weight) of NH$_4$OH (Showa Chemical Co., Lot. number 111024) was added with a pipette and mixed by stirring for about 5 minutes. Afterwards the second cyanoacrylate monomer, 32 ml of n-butyl cyanoacrylate monomer (nBCA, Chemence Co.), was added into the NH$_4$OH solution drop by drop and mixed by continuous stirring for about 0.5 hour.

The resulting nBCA polymer, namely Thickening Agent B, was decanted and dried in the vacuum oven at 65° C. for 8 hours. The molecular weight of nBCA polymer was measured with a gel permeation chromatography (GPC). Consequently, the molecular weight of nBCA polymer, i.e. Thickening Agent B is 41,200.

EXAMPLE 5

Preparation of Adhesive C

The first cyanoacrylate monomer, 285 g of 2-octyl cyanoacrylate monomer (2-OCA, the viscosity thereof is 6 cP at 20° C.), was poured into a 1 liter round bottom flask on a heater/mixer and stirred at 200 rpm. 15 g of Thickening Agent B prepared as described in Example 4 was then added slowly into the flask. After this, they were mixed at 100° C. for 60 minutes to form Adhesive C. The viscosity of the Adhesive C was measured with a capillary viscometer. The viscosity of the Adhesive C is 31 cP at 20° C.

EXAMPLE 6

Preparation of Adhesive D

The first cyanoacrylate monomer, 285 g of 2-octyl cyanoacrylate monomer (2-OCA, the viscosity thereof is 6 cP at 20° C.), was poured into a 1 liter round bottom flask on a heater/mixer and stirred at 200 rpm. 15 g of Thickening Agent B prepared as described in Example 4 was then added slowly into the flask. 15 g of tributyl 2-acetylcitrate was also added slowly subsequently, and then all were mixed at 100° C. for 60 minutes to form Adhesive D. The viscosity of the Adhesive D was measured with a capillary viscometer. The viscosity of the Adhesive D is 48 cP at 20° C.

EXAMPLE 7

Accelerated Aging Test to Check the Stability of Adhesive B 0.8 ml of Adhesive B sample was placed in each aluminum tube and sealed. A total of 300 Adhesive B samples were prepared for the execution of the testing. Those Adhesive B samples were randomly separated into 5 groups (Group 1-5) consisting of 60 samples/each. Those samples were aged in an Environmental Chamber at 60° C. to simulate various aging time at 20° C. The results are shown in Table 1.

TABLE 1

|  | Group | | | | |
| --- | --- | --- | --- | --- | --- |
|  | 1 | 2 | 3 | 4 | 5 |
| Accelerated Aging Equivalence (month) | 0 | 6 | 12 | 18 | 24 |
| Absolute Viscosity (cP) | 39 | 42 | 48 | 52 | 55 |
| Wound Closure Strength (N) | 9.2 | 8.7 | 8.7 | 8.3 | 8.1 |

EXAMPLE 8

Wound Closure Strength Test of Adhesive B

After aging test (Example 7), the samples were tested for their wound closure strength according to ASTM F2458 wound closure strength test. In this test, a thin layer of adhesive sample was applied on a piece of porcine skin specimen with a cut in the middle to simulate wound. Then, the force to pull the wound apart was measured.

Sufficient Adhesive B was first applied uniformly on a 2.5 cm×1.0 cm area adjacent to the cut to bond 2 pieces of porcine skins together. 10 sets of specimens were prepared. They were then placed in a sealed plastic bag and conditioned in 30±1° C. for 1 hr±15 min. Once the adhesive was cured, the specimens were allowed to cool to room temperature and were clamped between the upper and lower jaws of a universal test machine. The specimens were tested at a crosshead speed of 250 mm/min until failure. Both failure mode and peak load were recorded. The results of the wound closure strength test are shown in Table 1.

As seen from Table 1, the viscosity of Adhesive B increased as time goes by, but the wound closure strength thereof reduced slightly and possesses 8.1N after 24 months' aging. Thus, the adhesive provided by the present invention can prevent cyanoacrylate monomer from premature polymerization and has a desirable viscosity for convenient application. In addition, it also maintains appropriate wound closure strength for a long period of time.

EXAMPLE 9

Preparation of Thickening Agent C

For preparation of the accelerator, 1800 ml of deionized water was first placed in a 2000 ml beaker, and then 5 g (0.3% by weight) ethanol (Echo Chemical Co.) was added and mixed by stifling for about 5 minutes. Afterwards the second cyanoacrylate monomer, 32 ml of n-butyl cyanoacrylate monomer (nBCA, Chemence Co.), was added into the ethanol solution drop by drop and mixed by continuous stirring for about 0.5 hour.

The resulting nBCA polymer, namely Thickening Agent C, was decanted and dried in the vacuum oven at 65° C. for 8 hours. The molecular weight of nBCA polymer was measured with a gel permeation chromatography (GPC). Consequently, the molecular weight of nBCA polymer, i.e. Thickening Agent C, is 64,300.

EXAMPLE 10

Preparation of Adhesive E

The first cyanoacrylate monomer, 285 g of 2-octyl cyanoacrylate monomer (2-OCA, the viscosity thereof is 6 cP at 20° C.), was poured into a 1 liter round bottom flask on a heater/mixer and stirred at 200 rpm. 15 g of Thickening Agent C prepared in Example 9 was then added slowly into the flask. After this, they were mixed at 100° C. for 60 minutes to form Adhesive E. The viscosity of the Adhesive E was measured with a capillary viscometer. The viscosity of the Adhesive E is 47 cP at 20° C.

EXAMPLE 11

Preparation of Adhesive F

The first cyanoacrylate monomer, 285 g of 2-octyl cyanoacrylate monomer (2-OCA, the viscosity thereof is 6 cP at 20° C.), was poured into a 1 liter round bottom flask on a heater/mixer and stirred at 200 rpm. 15 g of Thickening Agent C prepared in Example 9 was then added slowly into the flask. 15 g of tributyl 2-acetylcitrate (ATBC, SAFC, Lot number MKBG8107V) was also added slowly subsequently. Then they were mixed at 100° C. for 60 minutes to form Adhesive F. The viscosity of the Adhesive F was measured with a capillary viscometer. The viscosity of the Adhesive F is 43 cP at 20° C.

EXAMPLE 12

Preparation of Thickening Agent D

For preparation of the accelerator, 1800 ml of deionized water was first placed in a 2000 ml beaker, and then 1.8 g (0.1% by weight) sodium bicarbonate (Sigma-Aldrich Co.) was added with a pipette and mixed by stirring for about 3 minutes. Afterwards the second cyanoacrylate monomer, 32 ml of n-butyl cyanoacrylate monomer (nBCA, Chemence Co.), was added into the sodium bicarbonate solution drop by drop and mixed by continuous stirring for about 0.5 hour.

The resulting nBCA polymer was decanted and rinsed several times with deionized water and then decanted again. The bicarbonate therein was neutralized with 0.1N HCl and then nBCA polymer was rinsed again with deionized water. The resulting product was dried in the vacuum oven at 65° C. for 8 hours to form Thickening Agent D. The molecular weight of the Thickening Agent D is 43,100.

EXAMPLE 13

Preparation of Adhesive G

The first cyanoacrylate monomer, 285 g of 2-octyl cyanoacrylate monomer (2-OCA, the viscosity thereof is 6 cP at 20° C.), was poured into a 1 liter round bottom flask on a heater/mixer and stirred at 200 rpm. 15 g of Thickening Agent D prepared in Example 12 was then added slowly into the flask. 15 g of tributyl 2-acetylcitrate (ATBC, SAFC, Lot number MKBG8107V) was also added slowly subsequently; and then all were mixed at 100° C. for 60 minutes to form Adhesive G. The viscosity of the Adhesive G was measured with a capillary viscometer. The viscosity of the Adhesive G is 31 cP at 20° C.

EXAMPLE 14

Accelerated Aging Test to Check the Stability of Adhesive G 0.8 ml of Adhesive G sample was placed in each aluminum tube and sealed. A total of 300 Adhesive G samples were prepared for the execution of the test. The Adhesive G samples were randomly separated into 5 groups (Group 6-10) consisting of 60 each. They were accelerately aged in an Environmental Chamber at 60° C. to simulate various aging time at 20° C. The results are shown in Table 2.

TABLE 2

| | Group | | | | |
| --- | --- | --- | --- | --- | --- |
| | 6 | 7 | 8 | 9 | 10 |
| Accelerated Aging Equivalence (month) | 0 | 6 | 12 | 18 | 24 |
| Absolute Viscosity (cP) | 35 | 48 | 68 | 80 | 150 |
| Wound Closure Strength (N) | 9.6 | 8.9 | 7.5 | 6.1 | 4.2 |

EXAMPLE 15

Wound Closure Strength Test of Adhesive G

After aging test (Example 14), the samples were tested for their wound closure strength according to ASTM F2458 wound closure strength test as described in Example 8.

Sufficient Adhesive G was first applied uniformly on a 2.5 cm×1.0 cm area adjacent to the cut to bond 2 pieces of porcine skins together. 10 sets of specimens were prepared. They were then placed in a sealed plastic bag and conditioned in 30±1° C. for 1 hr±15 min. Once the adhesive was cured, the specimens were allowed to cool to room temperature and were clamped between the upper and lower jaws of a universal test machine. The specimens were tested at a crosshead speed of 250 mm/min until failure. Both failure mode and peak load were recorded. The results of the wound closure strength test are shown in Table 2.

Referring to the results shown in Tables 1 and 2, the wound closure strength of Adhesive G has been reduced to 7.5N after 12 months' aging, and 4.2N after 24 months' aging. The adhesive thickened by polycyanoacrylate, which was prepared by conventional accelerators exhibits premature polymerization in a cyanoacrylate monomer adhesive due to its residual accelerators. Owing to this premature polymerization of adhesive substrate, either the wound bonding strength is reduced or the shelf life is shortened. However, with the thickening agent prepared by the ammonium hydroxide or alcohol provided by the present invention, the premature polymerization can be reduced and the adhesive having excellent properties can be used for various medical applications.

What is claimed is:

1. A method of making an adhesive composition, comprising the steps of:
   (a) providing an adhesive substrate, the adhesive substrate comprising at least a first cyanoacrylate monomer;
   (b) providing a thickening agent, the thickening agent comprising at least a polycyanoacrylate, wherein the polycyanoacrylate is prepared by a method comprising the steps of:
      providing a second cyanoacrylate monomer;
      adding an aqueous solution of ammonium hydroxide or alcohol into the second cyanoacrylate monomer to initiate polymerization and forming a polymer of the second cyanoacrylate monomer; and
      heating and drying the polymer of the second cyanoacrylate monomer at 30° C.~100° C. to remove the ammonium hydroxide or the alcohol; and
   (c) mixing the thickening agent with the adhesive substrate.

2. The method according to claim 1, wherein the first cyanoacrylate monomer or the second cyanoacrylate monomer is selected from the group consisting of alkyl 2-cyanoacrylate, cycloalkyl-2-cyanoacrylate, fluoroalkyl-2-cyanoacrylate, fluorocycloalkyl-2-cyanoacrylate, alkoxyalkyl-2-cyanoacrylate, alkoxycycloalkyl-2-cyanoacrylate, fluoroalkoxyalkyl-2-cyanoacrylate, and mixtures of two or more thereof.

3. The method according to claim 2, wherein the first cyanoacrylate monomer or the second cyanoacrylate monomer is selected from the group consisting of methyl 2-cyanoacrylate, ethyl 2-cyanoacrylate, n-propyl 2-cyanoacrylate, iso-propyl 2-cyanoacrylate, n-butyl 2-cyanoacrylate, iso-butyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate, 2-propoxyethyl 2-cyanoacrylate, and mixtures of two or more thereof.

4. The method according to claim 1, wherein step (c) further comprises adding at least a plasticizer and then mixing.

5. The method according to claim 4, wherein the plasticizer is selected from the group consisting of citric esters, glycerol esters, sebacic esters, fatty acid esters, cellulose esters, polyethylene glycol ethers, and mixtures of two or more thereof.

6. The method according to claim 5, wherein the plasticizer is tributyl 2-acetylcitrate.

7. The method according to claim 4, wherein step (c) further comprises adding a colorant, a free radical stabilizer or an anionic stabilizer and then mixing.

8. The method according to claim 1, wherein the thickening agent is about 0.5-25% by weight based on the total weight of the adhesive composition.

9. The method according to claim 8, wherein the thickening agent is about 1-10% by weight based on the total weight of the adhesive composition.

10. The method according to claim 9, wherein the thickening agent is about 1-5% by weight based on the total weight of the adhesive composition.

11. The method according to claim 1, wherein the aqueous solution of ammonium hydroxide is about 0.001-1% by weight.

12. The method according to claim 11, wherein the weight ratio of ammonium hydroxide to the second cyanoacrylate monomer is about 1:10000 to about 1:100.

13. The method according to claim 12, wherein the weight ratio of ammonium hydroxide to the second cyanoacrylate monomer is about 1:10000 to about 1:500.

14. The method according to claim 1, wherein the aqueous solution of alcohol is selected from the group consisting of methanol, ethanol, n-propanol, n-butanol, and mixtures thereof.

15. The method according to claim 14, wherein the aqueous solution of alcohol is about 0.1-1.5% by weight.

16. The method according to claim 15, wherein the aqueous solution of alcohol is the aqueous solution of ethanol.

17. The method according to claim 16, wherein the weight ratio of the alcohol to the second cyanoacrylate monomer is about 1:5000 to about 1:100.

18. The method according to claim 17, wherein the weight ratio of the alcohol to the second cyanoacrylate monomer is about 1:5000 to about 1:200.

19. The method according to claim 1, further comprising a step (d) of sterilizing the mixture of the thickening agent and the adhesive substrate.

20. An adhesive composition made by the method of claim 1.

* * * * *